US00PP25251P2

(12) United States Plant Patent
Wain

(10) Patent No.: US PP25,251 P2
(45) Date of Patent: Jan. 27, 2015

(54) ***CHRYSANTHEMUM* PLANT NAMED 'FIMMSUNPIBICO'**

(50) Latin Name: *Chrysanthemum×morifolium*
Varietal Denomination: Fimmsunpibico

(71) Applicant: Peter Wain, Locks Heath (GB)

(72) Inventor: Peter Wain, Locks Heath (GB)

(73) Assignee: Fides B.V., De Lier (NL)

( * ) Notice: Subject to any disclaimer, the term of this patent is extended or adjusted under 35 U.S.C. 154(b) by 139 days.

(21) Appl. No.: 13/815,199

(22) Filed: Feb. 8, 2013

(51) Int. Cl.
*A01H 5/00* (2006.01)

(52) U.S. Cl.
USPC ..... Plt./286

(58) Field of Classification Search
USPC ..... Plt./286
See application file for complete search history.

*Primary Examiner* — Annette Para
(74) *Attorney, Agent, or Firm* — C. A. Whealy

(57) ABSTRACT

A new and distinct cultivar of *Chrysanthemum* plant named 'Fimmsunpibico', characterized by its compact, upright to outwardly spreading and uniformly mounded plant habit; freely branching habit; dense and full plant habit; uniform and freely flowering habit; medium-sized decorative inflorescences with pink and red purple bi-colored ray florets; late August flowering response under natural season conditions; and good garden performance.

1 Drawing Sheet

Botanical designation: *Chrysanthemum×morifolium.*
Cultivar denomination: 'FIMMSUNPIBICO'.

BACKGROUND OF THE INVENTION

The present invention relates to a new and distinct *Chrysanthemum* plant, botanically known as *Chrysanthemum×morifolium*, commercially grown as a garden *Chrysanthemum* and hereinafter referred to by the name 'Fimmsunpibico'.

The new *Chrysanthemum* plant is a product of a planned breeding program conducted by the Inventor in Fareham, Hampshire, United Kingdom. The objective of the breeding program is to create new early-flowering garden *Chrysanthemum* plants with numerous attractive inflorescences.

The new *Chrysanthemum* plant originated from a cross-pollination made in January, 2007 by the Inventor in Fareham, Hampshire, United Kingdom of a proprietary selection of *Chrysanthemum×morifolium* identified as code number 3113, not patented, as the female, or seed, parent with a proprietary selection of *Chrysanthemum×morifolium* identified as code number 3012, not patented, as the male, or pollen, parent. The new *Chrysanthemum* plant was discovered and selected by the Inventor as a single flowering plant from within the progeny of the stated cross-pollination in a controlled greenhouse environment in Fareham, Hampshire, United Kingdom in September, 2007.

Asexual reproduction of the new *Chrysanthemum* by terminal vegetative cuttings was first conducted in Fareham, Hampshire, United Kingdom in December, 2007. Asexual reproduction by terminal vegetative cuttings has shown that the unique features of this new *Chrysanthemum* are stable and reproduced true to type in successive generations.

SUMMARY OF THE INVENTION

Plants of the new *Chrysanthemum* have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Fimmsunpibico'. These characteristics in combination distinguish 'Fimmsunpibico' as a new and distinct *Chrysanthemum* plant:

1. Compact, upright to outwardly spreading and uniformly mounded plant habit.
2. Freely branching habit; dense and full plant habit.
3. Uniform and freely flowering habit.
4. Medium-sized decorative inflorescences with pink and red purple bi-colored ray florets.
5. Plants flower under natural season conditions during the last week of August in the United Kingdom.
6. Good garden performance.

Plants of the new *Chrysanthemum* can be compared to plants of the female parent selection. Plants of the new *Chrysanthemum* differ from plants of the female parent selection, in the following characteristics:

1. Plants of the new *Chrysanthemum* have slightly smaller inflorescences than plants of the female parent selection under natural season conditions.
2. Plants of the new *Chrysanthemum* and the female parent selection differ in ray floret color as plants of the female parent selection have pink-colored ray florets.

Plants of the new *Chrysanthemum* can be compared to plants of the male parent selection. Plants of the new *Chrysanthemum* differ from plants of the male parent selection, in the following characteristics:

1. Plants of the new *Chrysanthemum* have larger inflorescences than plants of the male parent selection.
2. Plants of the new *Chrysanthemum* and the male parent selection differ in ray floret color as plants of the male parent selection have white-colored ray florets.

Plants of the new *Chrysanthemum* can be compared to plants of *Chrysanthemum×morifolium* 'Yogigi Pink', disclosed in U.S. Plant Pat. No. 19,666. In side-by-side comparisons conducted in Fareham, Hampshire, United Kingdom, plants of the new *Chrysanthemum* differed from plants of 'Yogigi Pink' in the following characteristics:

1. Plants of the new *Chrysanthemum* were more upright than plants of 'Yogigi Pink'.
2. Plants of the new *Chrysanthemum* had larger inflorescences than plants of 'Yogigi Pink'.
3. Plants of the new *Chrysanthemum* flowered about one week earlier than plants of 'Yogigi Pink' under natural season conditions.

BRIEF DESCRIPTION OF THE PHOTOGRAPH

The accompanying photograph illustrates the overall appearance of the new *Chrysanthemum* showing the colors as true as it is reasonably possible to obtain in colored reproductions of this type. Colors in the photograph may differ slightly from the color values cited in the detailed botanical description which accurately describe the colors of the new *Chrysanthemum.*

The photograph comprises a top perspective view of a typical flowering plant of 'Fimmsunpibico' grown in a container.

DETAILED BOTANICAL DESCRIPTION

The aforementioned photograph and following observations and measurements describe plants grown during the late summer and early autumn in 19-cm containers in an outdoor nursery in Fareham, Hampshire, United Kingdom and under cultural practices typical of commercial garden *Chrysanthemum* production. During the production of the plants, day temperatures ranged from 10° C. to 25° C., night temperatures ranged from 5° C. to 15° C. and light levels ranged from 400 to 2,500 joules. Plants were pinched one time and were about 14 weeks old when the photograph and detailed description were taken. In the following description, color references are made to The Royal Horticultural Society Colour Chart, Fifth Edition, except where general terms of ordinary dictionary significance are used.

Botanical classification: *Chrysanthemum×morifolium* 'Fimmsunpibico'.

Parentage:

*Female, or seed, parent.*—Proprietary selection of *Chrysanthemum×morifolium* identified as code number 3113, not patented.

*Male, or pollen, parent.*—Proprietary selection of *Chrysanthemum×morifolium* identified as code number 3012, not patented.

Propagation:

*Type.*—Terminal vegetative cuttings.

*Time to initiate roots, summer.*—About ten days at temperatures of about 21° C.

*Time to initiate roots, winter.*—About twelve days at temperatures of about 21° C.

*Time to produce a rooted young plant, summer.*—About three weeks at temperatures of about 21° C.

*Time to produce a rooted young plant, winter.*—About four weeks at temperatures of about 21° C.

*Root description.*—Fine, fibrous; light brown in color.

*Rooting habit.*—Freely branching; medium density.

Plant description:

*Plant and growth habit.*—Herbaceous decorative-type garden *Chrysanthemum*; compact with stems upright to outwardly spreading giving a uniformly mounded appearance to the plant; numerous lateral branches and relatively short internodes, dense and full plant habit; moderately vigorous growth habit.

*Plant height.*—About 28 cm.

*Plant width.*—About 43.5 cm.

*Branching habit.*—Freely branching habit, about twelve lateral branches develop after removal of terminal apex (pinching); each primary lateral with numerous secondary laterals.

*Lateral branches.*—Length: About 20 cm. Diameter: About 4 mm. Internode length: About 1 cm. Strength: Strong, flexible. Aspect: About 75° from stem. Texture: Fine pubescence. Color: Close to 146B.

*Leaves.*—Arrangement: Alternate, simple. Length: About 5 cm. Width: About 3 cm. Shape: Palmately-lobed; roughly ovate. Apex: Apiculate to mucronate. Base: Obtuse with truncate tendencies. Margin: Palmately lobed, sinuses between lateral lobes parallel to divergent; slightly dentate. Texture, upper surface: Fine pubescence, sparse. Texture, lower surface: Fine pubescence; veins prominent. Color: Developing leaves, upper surface: Close to 137A. Developing leaves, lower surface: Close to 138B. Fully expanded leaves, upper surface: Close to 137B; venation, close to 147C. Fully expanded leaves, lower surface: Close to 138B; venation, close to 146C. Petiole: Length: About 1 cm. Diameter: About 2 mm. Texture, upper and lower surfaces: Fine pubescence. Color, upper surface: Close to 146A. Color, lower surface: Close to 146B.

Inflorescence description:

*Form and flowering habit.*—Decorative inflorescence form with oblanceolate-shaped ray florets; inflorescences borne on terminals above and beyond the foliar plane; disc and ray florets arranged acropetally on a capitulum; freely flowering habit with about 27 inflorescences developing per lateral branch and about 810 inflorescences developing per plant.

*Fragrance.*—Fragrant; pungent, herbaceous.

*Flowering response.*—Early flowering habit, plants exposed to natural season conditions begin flowering the last week of August in the United Kingdom; with photoinductive conditions, response time is about 33 days.

*Inflorescence longevity.*—Inflorescences maintain good color and substance for about three to five weeks on the plant; inflorescences persistent.

*Inflorescence buds.*—Height: About 5 mm. Diameter: About 7 mm. Shape: Oblate. Color: Close to 144B.

*Inflorescence height.*—About 1.5 cm.

*Inflorescence diameter.*—About 4 cm.

*Disc diameter.*—About 1 cm.

*Receptacles.*—Height: About 3 mm. Diameter: About 4 mm. Shape: Hemispherical, pointed. Color: Close to 145C.

*Ray florets.*—Orientation: Initially upright, then about 80° from vertical. Length: About 2.2 cm. Width: About 6 mm. Shape: Oblanceolate. Apex: Emarginate. Base: Fused into a short tube. Margin: Entire. Texture, upper and lower surfaces: Smooth, glabrous. Number of ray florets per inflorescence: About 178 arranged in about 13 whorls. Color: When opening, upper surface: Close to 69C. When opening, lower surface: Close to 69C flushed with close to 72C. Fully opened, upper surface: Close to 69D; color becoming closer to 76D with development. Fully opened, lower surface: Close to 69D flushed with close to 75B; color becoming closer to N155C flushed with close to 69C with development.

*Disc florets*.—Shape: Tubular, elongated. Length: About 5 mm. Diameter: About 1 mm. Number of disc florets per inflorescence: About ten. Color, immature: Apex: Close to 15C. Mid-section: Close to 142D. Base: Close to 155D. Color, mature: Apex: Close to 15D. Mid-section: Close to 142D. Base: Close to 155D.

*Phyllaries*.—Number of phyllaries per inflorescence: About 26 arranged in about four whorls. Length: About 7 mm. Width: About 3 mm. Shape: Lanceolate. Apex: Bluntly acute. Base: Truncate, fused. Margin: Entire. Texture, upper surface: Smooth, glabrous; waxy. Texture, lower surface: Fine pubescence; waxy. Color, upper surface: Close to 138A. Color, lower surface: Close to 137B.

*Peduncles*.—Length, terminal peduncle: About 5.5 cm. Diameter, terminal peduncle: About 1 mm. Angle: Erect to about 35° from vertical. Strength: Moderately strong, flexible. Texture: Fine pubescence. Color: Close to 146B.

*Reproductive organs*.—Androecium: None observed. Gynoecium (present on ray and disc florets): Pistil length: About 7 mm. Stigma shape: Bi-parted. Stigma color: Close to 12A. Style length: About 4 mm. Style color: Close to 1D. Ovary color: Close to 157D.

*Seeds and fruits*.—Seed and fruit production has not been observed on plants of the new *Chrysanthemum*.

Disease & pest resistance: Resistance to pathogens and pests common to *Chrysanthemum* plants has not been observed on plants of the new *Chrysanthemum* grown under commercial conditions.

Garden performance: Plants of the new *Chrysanthemum* have demonstrated good garden performance and to tolerate temperatures from about 0° C. to about 35° C.

It is claimed:

1. A new and distinct *Chrysanthemum* plant named 'Fimmsunpibico' as illustrated and described.

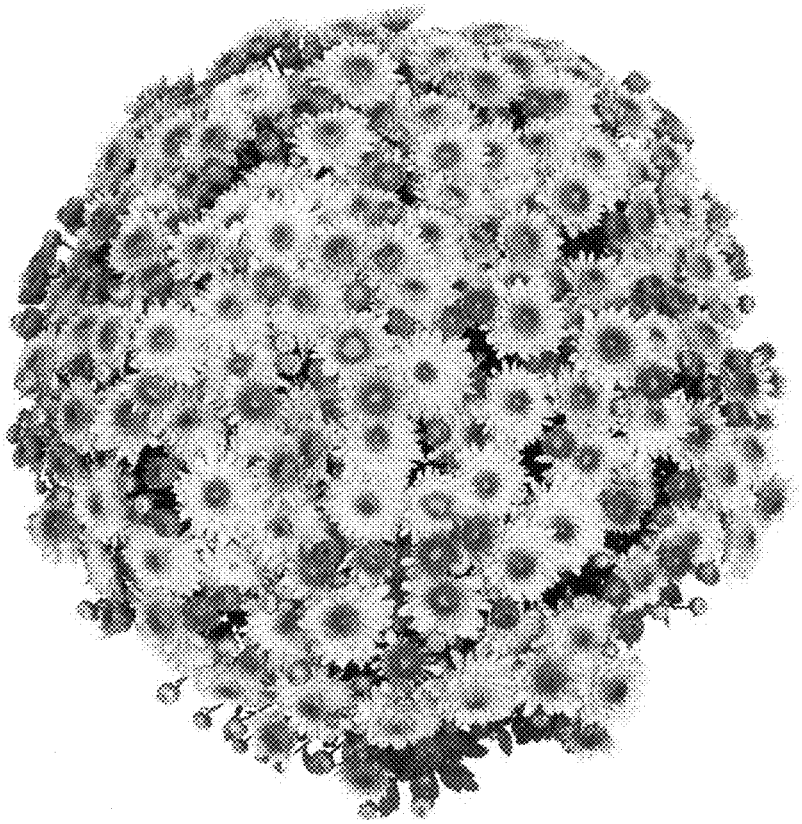

* * * * *